(12) United States Patent
Stanford et al.

(10) Patent No.: US 11,013,451 B2
(45) Date of Patent: May 25, 2021

(54) MARKER-LESS MONITORING OF MOVEMENT DISORDERS

(71) Applicant: BRIGHAM YOUNG UNIVERSITY, Provo, UT (US)

(72) Inventors: Nathan Stanford, Provo, UT (US); Steven Charles, Provo, UT (US)

(73) Assignee: Brigham Young University, Provo, UT (US)

( * ) Notice: Subject to any disclaimer, the term of this patent is extended or adjusted under 35 U.S.C. 154(b) by 277 days.

(21) Appl. No.: 14/858,712

(22) Filed: Sep. 18, 2015

(65) Prior Publication Data

US 2016/0081609 A1   Mar. 24, 2016

Related U.S. Application Data

(60) Provisional application No. 62/052,730, filed on Sep. 19, 2014.

(51) Int. Cl.
| | |
|---|---|
| *A61B 5/00* | (2006.01) |
| *A61B 5/11* | (2006.01) |
| *G16H 50/30* | (2018.01) |
| *G16H 40/63* | (2018.01) |
| *G16H 50/20* | (2018.01) |
| *G16H 10/60* | (2018.01) |

(52) U.S. Cl.
CPC .............. *A61B 5/4082* (2013.01); *A61B 5/11* (2013.01); *A61B 5/7275* (2013.01); *G16H 40/63* (2018.01); *G16H 50/20* (2018.01); *G16H 50/30* (2018.01); *A61B 5/742* (2013.01); *G16H 10/60* (2018.01)

(58) Field of Classification Search
None
See application file for complete search history.

(56) References Cited

U.S. PATENT DOCUMENTS

| | | | |
|---|---|---|---|
| 7,257,237 B1 | 8/2007 | Luck et al. | |
| 7,457,439 B1 | 11/2008 | Madsen et al. | |
| 7,804,998 B2 | 9/2010 | Mundermann et al. | |
| 8,023,726 B2 | 9/2011 | Sundaresan et al. | |
| 8,325,984 B2 | 12/2012 | Lee et al. | |
| 8,355,529 B2 | 1/2013 | Wu et al. | |
| 8,388,555 B2* | 3/2013 | Panken | A61N 1/36071 600/587 |
| 8,527,217 B2 | 9/2013 | Moodie | |
| 8,542,910 B2 | 9/2013 | Leyvand et al. | |
| 8,587,583 B2 | 11/2013 | Newcombe et al. | |

(Continued)

*Primary Examiner* — Patrick Fernandes
*Assistant Examiner* — Benjamin S Melhus
(74) *Attorney, Agent, or Firm* — Brake Hughes Bellermann LLP (57) ABSTRACT

A system for monitoring a movement disorder includes a movement detector configured to track at least one point of reference in three dimensions, and a computing device communicatively coupled with the movement detector. The computing device is configured to receive movement data associated with the at least one point of reference over a period of time, perform a kinematic data analysis based on the movement data, compute a weighted score using the kinematic data analysis, compute a trend based on historical movement data, the weighted score and the trend being associated with the movement disorder, and display the weighted score, the trend and the movement data on a display associated with the computing device.

20 Claims, 5 Drawing Sheets

(56) References Cited

U.S. PATENT DOCUMENTS

| | | |
|---|---|---|
| 8,588,465 B2 | 11/2013 | Geiss |
| 8,644,552 B2 | 2/2014 | Han et al. |
| 9,408,561 B2* | 8/2016 | Stone .................... A61B 5/112 |
| 9,524,424 B2* | 12/2016 | Greene .................. A61B 5/112 |
| 2004/0015103 A1* | 1/2004 | Aminian ............... A61B 5/1116<br>600/595 |
| 2007/0276270 A1* | 11/2007 | Tran ....................... A61B 5/002<br>600/508 |
| 2009/0306484 A1* | 12/2009 | Kurtz .................... A61B 5/442<br>600/300 |
| 2010/0030119 A1* | 2/2010 | McNames ............ A61B 5/1101<br>600/595 |
| 2010/0111370 A1 | 5/2010 | Black et al. |
| 2010/0145236 A1 | 6/2010 | Greenberg et al. |
| 2010/0152622 A1* | 6/2010 | Teulings .............. A61B 5/1101<br>600/595 |
| 2010/0268551 A1 | 10/2010 | Mcnames et al. |
| 2011/0205337 A1 | 8/2011 | Ganapathi et al. |
| 2012/0163675 A1 | 6/2012 | Joo et al. |
| 2013/0028489 A1 | 1/2013 | Tracton et al. |
| 2013/0123645 A1* | 5/2013 | Stimson ................ A61B 5/742<br>600/476 |
| 2013/0123666 A1 | 5/2013 | Giuffrida et al. |
| 2013/0123684 A1 | 5/2013 | Giuffrida et al. |
| 2013/0289449 A1* | 10/2013 | Stone .................... A61B 5/004<br>600/595 |
| 2013/0324857 A1* | 12/2013 | Kurillo ................ A61B 5/1127<br>600/476 |
| 2014/0024971 A1* | 1/2014 | Bunn ....................... A61B 5/11<br>600/595 |
| 2014/0072175 A1 | 3/2014 | Hasler et al. |
| 2014/0074180 A1* | 3/2014 | Heldman ........... A61N 1/36139<br>607/45 |
| 2014/0100486 A1* | 4/2014 | Alberts ................ A61B 5/1106<br>600/595 |
| 2014/0142439 A1* | 5/2014 | French ................ A61B 5/4088<br>600/483 |
| 2014/0153794 A1* | 6/2014 | Varaklis ............... A61B 5/1128<br>382/128 |
| 2014/0276095 A1* | 9/2014 | Griggs ................. A61B 5/1121<br>600/476 |
| 2014/0276130 A1* | 9/2014 | Mirelman .............. A61B 5/162<br>600/483 |
| 2014/0371544 A1* | 12/2014 | Wu ......................... G06T 7/262<br>600/301 |
| 2014/0371599 A1* | 12/2014 | Wu ....................... A61B 5/0077<br>600/476 |
| 2015/0092980 A1* | 4/2015 | Folmer ................ A61B 5/4866<br>382/103 |
| 2015/0348429 A1* | 12/2015 | Dalal .................... A61B 5/1114<br>434/258 |
| 2016/0095546 A1* | 4/2016 | Sahasrabudhe ...... A61B 5/7475<br>600/301 |
| 2016/0262685 A1* | 9/2016 | Wagner ................ A61B 5/1101 |
| 2017/0086712 A1* | 3/2017 | Mauro ............... G06K 9/00355 |
| 2017/0293805 A1* | 10/2017 | Kontschieder ........ G06F 16/783 |
| 2018/0078843 A1* | 3/2018 | Tran ...................... A61B 5/681 |
| 2020/0060602 A1* | 2/2020 | Wagner ............... A61B 5/0077 |

* cited by examiner

MARKER-LESS MONITORING OF MOVEMENT DISORDERS

This application claims the benefit of U.S. Provisional Patent Application 62/052,730 filed on Sep. 19, 2014, entitled "MARKER-LESS MONITORING OF MOVEMENT DISORDERS", the entire contents of which are incorporated in their entirety herein by reference.

FIELD

Embodiments relate to systems and methods configured to capture, record and trend tremor measurements over time.

BACKGROUND

Disorders that can benefit from these systems can include, but are not limited to, Parkinson's Disease, Amyotrophic Lateral Sclerosis, Huntington's Disease, Essential Tremor Traumatic Brain Injury and/or the like. This includes roughly 1 million Americans currently living with Parkinson's Disease, 10 million Americans with Essential Tremor 1.7 million people who suffered a Traumatic Brain Injury accident last year in America. There are many other clinical and research applications where the embodiments can be used for tracking and interpreting upper limb movement disorder.

Tracking and interpreting an upper-limb movement disorder, or tremor, in a quantified way typically employs using a system with accelerometers and/or markers attached to a person's body. There are many people who currently live with movement disorders and have no effective way to track progression of the disease outside of periodic qualitative review from a caretaker or practitioner who specializes in movement disorders. This physician makes a diagnosis by a subjective metric, which utilizes a visual based rating system (such as the TETRAS, WHIGET and Fahn-Tlosa-Marin scale) that fails to capture fine movement changes or irregularities in a patient's tremor over time. Symptomatic patients can exhibit a variety of movements that are characterized by the disorder itself but are adapted to the physiological constraints of the patient.

SUMMARY

In a general aspect, a system for monitoring a movement disorder is disclosed. The system for monitoring a movement disorder includes a movement detector configured to track at least one point of reference in three dimensions, and a computing device communicatively coupled with the movement detector. The computing device is configured to receive movement data associated with the at least one point of reference over a period of time, perform a kinematic data analysis based on the movement data, compute a weighted score using the kinematic data analysis, compute a trend based on historical movement data, the weighted score and the trend being associated with the movement disorder, and display the weighted score, the trend and the movement data on a display associated with the computing device.

In another general aspect, a computer implemented method is disclosed. The computer implemented method includes tracking at least one point of reference in three dimensions, receiving movement data associated with the at least one point of reference over a period of time, performing a kinematic data analysis based on the movement data, computing a weighted score using the kinematic data analysis, computing a trend based on historical movement data, the weighted score and the trend being associated with a movement disorder, and displaying the weighted score, the trend and the movement data on a display associated with a computing device.

In a still another general aspect, a non-transitory computer-readable storage medium having stored thereon computer executable program code which, when executed on a computer system, causes the computer system to perform steps is disclosed. The steps include tracking at least one point of reference in three dimensions, receiving movement data associated with the at least one point of reference over a period of time, performing a kinematic data analysis based on the movement data, computing a weighted score using the kinematic data analysis, computing a trend based on historical movement data, the weighted score and the trend being associated with a movement disorder, and displaying the weighted score, the trend and the movement data on a display associated with a computing device. Implementations can include one or more of the following features. For example, the movement detector can be a depth sensing camera. The at least one point of reference can include at least one of a finger, a plurality of fingers, a hand, a wrist, an arm, a head, a torso, and a leg. The at least one point of reference may not include an attached marker, and the at least one point of reference may not include an attached sensor. The computing device can be further configured to compute metrics including an amplitude, a frequency, and a velocity based on the kinematic data analysis. The computing device can include a dashboard implemented as an element of a software package. The dashboard can be configured to initiate and select test associated with at least one movement disorder, after a test has been completed, display results including at least the weighted score and the trend, and control access to a users data.

For example, the computing device can be configured to allow a user to generate a user profile including information associated with at least one movement disorder. The computing device can be configured to automatically generate at least one test plan based on the user profile. The computing device can be configured to compute an amplitude and a frequency based on the kinematic data analysis. The computing device can be configured to compute a displacement based on the amplitude. The weighted score can be calculated based on a weighted displacement and a weighted frequency.

BRIEF DESCRIPTION OF THE DRAWINGS

Example embodiments will become more fully understood from the detailed description given herein below and the accompanying drawings, wherein like elements are represented by like reference numerals, which are given by way of illustration only and thus are not limiting of the example embodiments and wherein.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DESCRIPTION

While example embodiments may include various modifications and alternative forms. It should be understood, however, that there is no intent to limit example embodiments to the particular forms disclosed, but on the contrary, example embodiments are to cover all modifications, equivalents, and alternatives.

There are two techniques used to track tremor. In a first technique a motion capture system(s) can utilize markers. The markers can include accelerometers, pen-and-pencil and other manual tests. These systems include lasers, electromagnetic statements and some hybrid video visual products that used reflective markers to track movements (e.g., of a patient). Information collected using this system can be analyzed using prepackaged algorithms (e.g., using a software package or suite) in order to objectively characterize tremor or even diagnose tremor by characterization.

The second technique can utilize a sensor (e.g., a single three-axis accelerometer attached to a patient's hand) to transmit to a portable computing device (e.g., a tablet, laptop, and/or the like) that communicates with a networked computer. The sensor can have the potential to dampen tremor based on a mass of the sensor (e.g., the heavier the sensor the more likely tremor is dampened). Bulky sensors can also impede movement of extremities (e.g., fingers) in certain degrees of freedom and create unnatural and/or unintelligible artifacts in collected data. Further, one data point of motion can be tracked over time and usually is employed for the most distant part of the limb. Research in this field shows that people with any kind of upper limb movement disorders show non-uniform symptoms throughout the progression of their disorder. Thus a more comprehensive view of the disorder with more data points spread out over the different joints of the hand could demonstrate more effectively the status of the patient's condition.

A system according to example embodiments can use a marker-less system that gathers data (e.g., xyz coordinates and velocity vectors) associated with selected body parts. For example, data can be collected for fingers (e.g., all or a portion of) and the hands, in addition to wrists, arms, head, torso, legs and/or voice. In other words, the system of the example embodiment can be configured to collect a lot of data over a relatively short period of time. This can allow for a much more complete picture of what a patient's tremor is actually doing over time. The data collected and the type of processing can allow for software (including system specific algorithms) to efficiently track the tremor in all degrees of freedom and other physiological variable such as voice that are affected. This data processing can then be compared to the tremor rating scales.

The system according to example embodiments can be cost effective as compared to conventional systems. For example, a depth sensing camera can be used to capture a user's movement disorder (e.g., at a low cost (e.g., $80-$250) depending on the desired camera). Conventional systems can be cost prohibitive (e.g., greater than $5000) and work on a closed system that is only accessible to patients who also have doctors that have also purchased the system.

In an example implementation, the system can be configured to allow for an objective, non-cumbersome and non-obtrusive mechanism for patients to accurately track and profile their movement disorder(s) over time. Further, the system can track multiple points of reference (e.g., on the human body). For example, the system can track ten fingers simultaneously as well as the hand and wrist. In another example implementation, the system can track lower limbs or even head and voice tremors. The combination of depth data and multiple points of reference give caretakers (e.g., a doctor) a more complete picture of a patient's tremor. According to example embodiments, gathering data associated with a patient's condition without the use of any external marker is possible.

Example embodiments may include a software suite and accompanying algorithms (described below) that can be configured to allow a user (e.g., patient) to track his or her movement disorder or other movement irregularity through the aide of a marker-less, motion capture system. This software suite can take the kinematic output data of a motion capture system and apply various algorithms (described below) to calculate measures and/or metrics related to movement, either in real time or as stored data files. Over time, such measures and/or metrics can allow for the creation of an effective map of a patient's movement disorder. The software may also be configured to log information regarding the time of day and medication levels (as input by the patient or a clinician) that can help a clinician provide further treatment.

In an example implementation, the software may take as its input the kinematic output data from depth-perceiving cameras that utilize a combination of depth data (e.g., points in 3D space) and optical (e.g., RGB) images. This data can allow the software system to produce a viable model of a patient's movement disorder both accurately and with high resolution. Some common depth sensing cameras that are currently on the market that would be potentially compatible with this software are the Leap Motion®, Microsoft Kinect®, Sony Camera®, Asus Xtion®, Mesa Imaging Swiss Ranger®, PMD Cam Cube®, and Primesense® cameras. The example software can use algorithms (described below) to process this data and produce measures and/or metrics that relate to movement disorders or tremors, where a tremor is most pronounced and how the tremor varies over time.

The information can be sent directly to the patient's computer and can be secured in their online profile. A patient can use the depth-sensing device with their personal computer or tablet and potentially an item or two that can aide in the analysis. From a measurement with these devices a measurement gauging the severity of the tremor can be extracted and saved for immediate viewing and access.

In an example implementation, the program can be configured to allow for a Natural User Interface (NUI) (e.g., a NUI is the equivalent to no touchscreen and no mouse or other input device) of the device to capture the individuals motions. This motion could be in the form of a movement disorder such as Parkinson's disease, Essential Tremor, bradykinesia, rigidity, or and other upper or lower body movement disorders.

Upper body movement disorders may be tracked, for example, with a table top version of the system and may be configured to allow for a real time analysis of the users movement disorder(s). In other words, a patient can view results directly following a measurement period. In example implementations, the system would not use a marking system (e.g., marker-less) for a regular test of a user's standing or kinetic tremor. The system may use a simple set up to do tests of everyday living which could use a small cup or utensil that could be tracked accurately with a small reflective item that would allow for easy analysis of the data on the item when in plain view of the camera.

Figure 1:
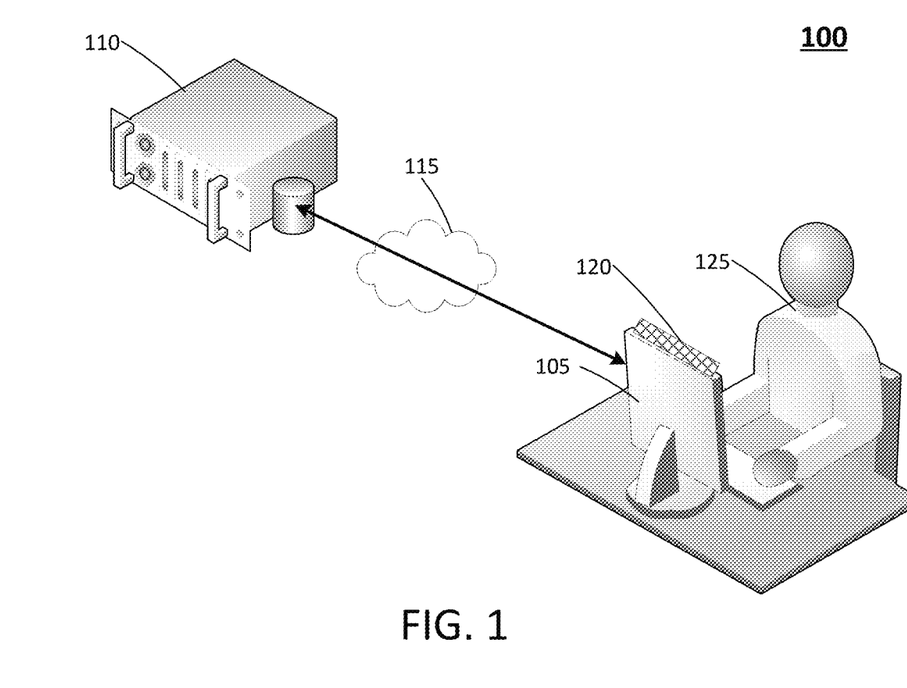
FIG. 1 is a block diagram of a system according to at least one example embodiment.

FIG. 1 is a block diagram of a system according to at least one example embodiment. As shown in FIG. 1, the system (or apparatus) 100 includes a computing device 105, a datacenter 110, a network 115, a movement detector 120 and a user or patient 125.

The computing device 105 may be any one of a desktop computer, a laptop computer, a tablet, a hand held device, and/or the like. The datacenter 110 may be a server, a data store, a database and/or the like. The network 115 may be an Internet, an Intranet, and/or a combination thereof. The movement detector 120 may be configured to measure, detect and or generate raw positional data (e.g., points in 3D space). The raw positional data can be analyzed to determine how the points change to compute metrics such as, but not limited to, amplitude, frequency, and velocity. Other metrics are contemplated and within the scope of this disclosure. The movement detector 120 may be a camera, a depth sensing camera, or a movement sensor. For example, the movement detector may be a Leap Motion®, Microsoft Kinect®, Sony® Camera, Asus Xtion®, Mesa Imaging Swiss Ranger®, PMD Cam Cube®, Primesense® cameras, and/or the like. Further, in an example implementation, the movement detector 120 can be under the hands of the patient in front of a display of the computing device 105. The movement detector 120 should have a clear field of view (e.g., to the body part) for the measurement to be taken. The user or patient 125 may be an individual afflicted with one of a tremor and/or other movement disorder.

The movement detector 120 is illustrated as being proximate to the computing device 105. However, example embodiments are not limited thereto. For example, the computing device 105 may be a network device associated with a cloud computing environment. The movement detector 120 may be communicatively coupled to the computing device using a wired or wireless protocol (e.g., internet protocol). Accordingly, the methods and techniques described herein may be implemented on a remote computing device coupled to the movement detector 120 in a location in which a patient is located. The patient may interact with the computing device 105 using a web browser on a user device (e.g., tablet, cell phone, laptop, and/or the like).

Figure 2:
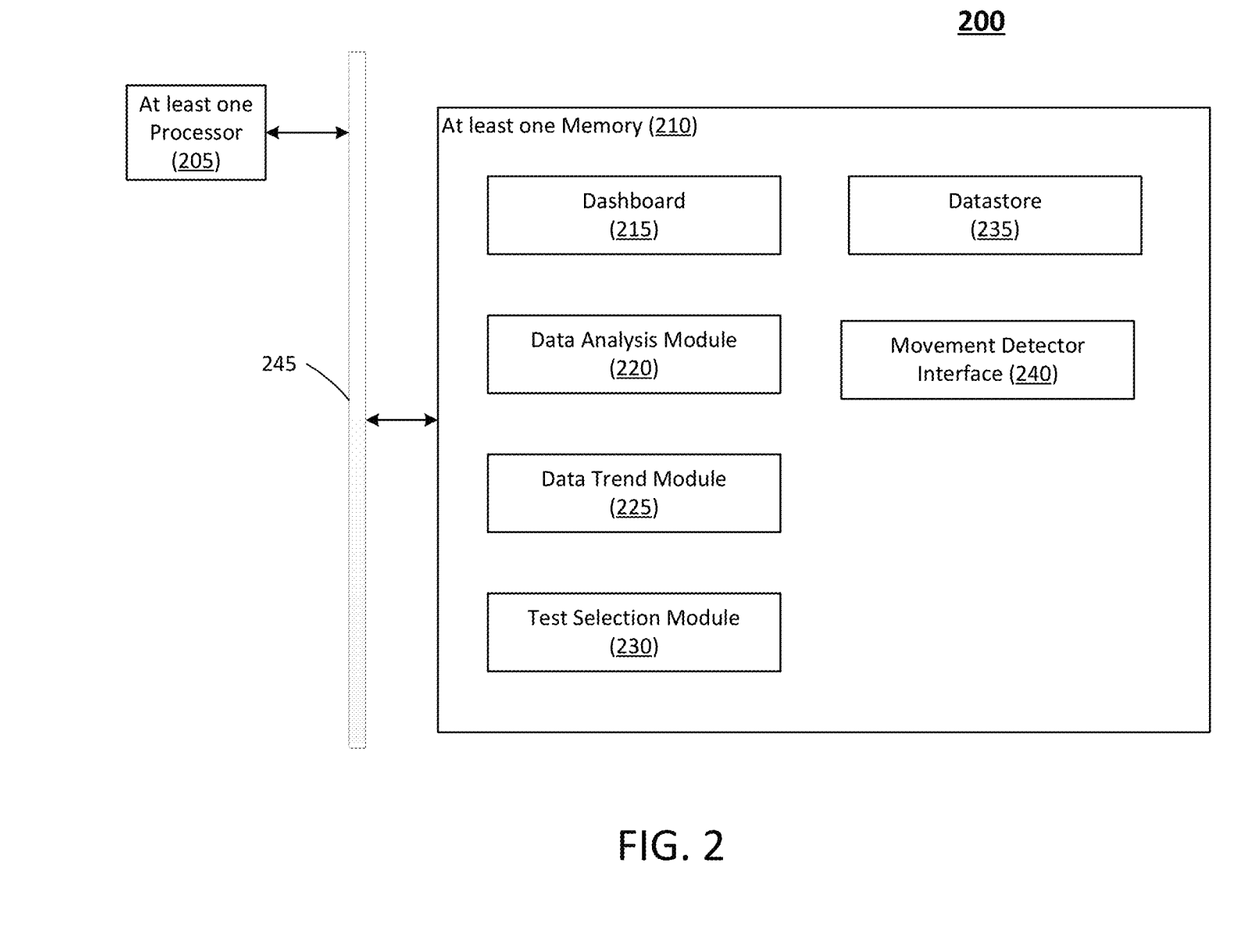
FIG. 2 is a block diagram of a system according to at least one example embodiment.

FIG. 2 is a block diagram of a system according to at least one example embodiment. As shown in FIG. 2, the system (or apparatus) 200 includes at least one processor 205 and at least one memory 210. The at least one processor 205 and the at least one memory 210 are communicatively coupled via bus 245. The system 200 may be, for example, an element of a computing device (e.g., a personal computer, a mobile device, a cloud computing device or a server).

In the example of FIG. 2, the system 200 may be at least one computing device and should be understood to represent virtually any computing device configured to perform the methods described herein. As such, the system 200 may be understood to include various standard components which may be utilized to implement the techniques described herein, or different or future versions thereof. By way of example, the system 200 is illustrated as including the at least one processor 205 (e.g., a silicon based processor), as well as the at least one memory 210 (e.g., a non-transitory computer readable storage medium) respectively.

Thus, the at least one processor 205 may be utilized to execute instructions stored on the at least one memory 210 (e.g., as a non-transitory computer readable medium), so as to thereby implement the various features and functions described herein, or additional or alternative features and functions. The at least one processor 105 and the at least one memory 210 may be utilized for various other purposes. For example, the at least one memory 210 may be understood to represent an example of various types of memory and related hardware and software which might be used to implement any one of the modules described herein. Systems and/or methods described below may include data and/or storage elements. The data and/or storage elements (e.g., data base tables) may be stored in, for example, the at least one memory 210.

As shown in FIG. 2, the at least one memory 210 includes a dashboard 215, a data analysis module 220, a data trend module 225, a test selection module 230, a datastore 235, and a movement detector interface 240.

In example implementations, the dashboard 215 can be can be configured to initiate and select tests and after any number of tests have been completed, the user can view results (e.g., graphs or numbers or ratings). The computed motions from the tests can be shown and the user can be able to input any additional data. The dashboard 215 can also be used by the user to modify what other people have access to their personal data as released by the user.

The data analysis module 220 can be configured to retrieve the raw data collected during a test and using an algorithm (e.g., to convert raw data to amplitude, frequency, and velocity data) to calculate a degree of tremor. The data analysis module 220 can also be configured to compare the data to one or more of the above mentioned standards. The data analysis module 220 can also be configured to generate graphs or other data for display. The data trend module 225 can be configured to compare stored and/or historical test data over a time period (e.g., as selected using the dashboard 215) and to generate a trend for display (e.g., as a graph). The test selection module 230 can be configured to select a test or test to be performed based on user input related to a type of affliction. The datastore 235 can be configured to store configuration data, profile data and test result data. The datastore 235 can be a secured data repository configured to require authorized access in order to protect patient privacy and/or protect against improper use of patient data.

The movement detector interface 240 can be configured to receive measurements from the movement detector 120 and convert the measurements to data for use by the system (e.g., data analysis module 220). The movement detector interface 240 may also be configured to perform or help perform a calibration routine associated with the movement detector. For example, the movement detector interface 240 can receive raw positional data (e.g., points in 3D space) from the movement detector 120 over a period of time. The raw positional data can be used to calculate metrics such as, but not limited to, amplitude, frequency, and velocity associated with movement (e.g., tremor) of the patient. The metrics can then be used by the data analysis module 220. The raw positional data and/or the calculated metrics can be stored in the datastore 235.

In an example implementation, a kinematic data analysis can be performed on the raw positional data. For example, the kinematic data analysis can be an analysis of the movement data to generate measures that summarize major aspects of a patient's movement. Kinematic data analysis can include, but is not limited to, summary statistics (e.g., mean, standard deviation, and the like), power spectrum, numerical derivatives (e.g., obtain velocity, acceleration, jerk, and the like), numerical integrals, the number frequency and quality of actions, as just a few examples.

In an example implementation, the raw positional data is converted to a signal power (or amplitude) at different frequencies. For example, an averaged power spectrum can be generated using Welsh's method (or approach) to spectral density estimation. In this example implementation, the primary tremor frequency is the frequency on this spectrum that corresponds with the maximum (or peak) amplitude.

Figure 3:
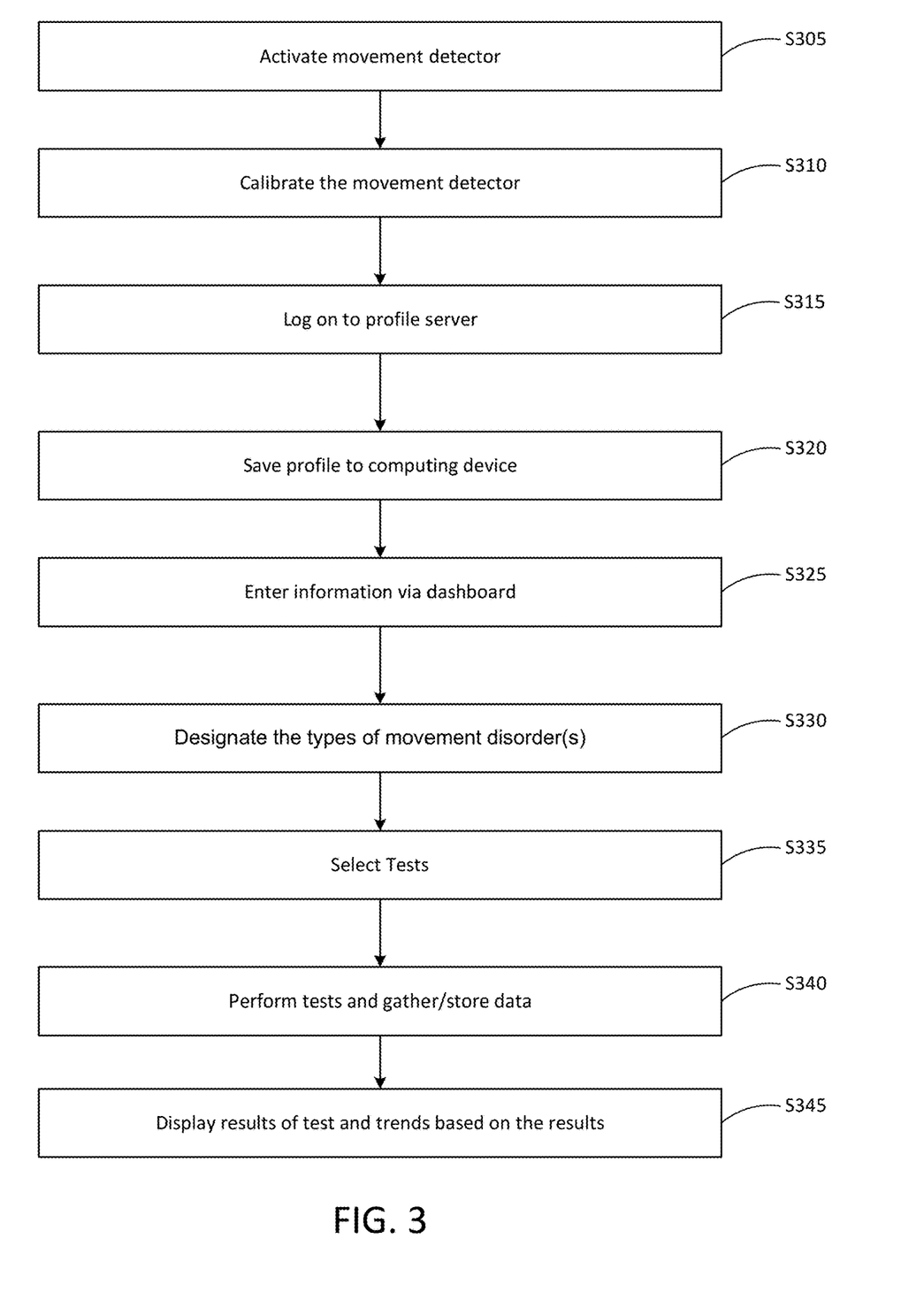
FIGS. 3-5 are flowcharts of methods according to example embodiments.
Figure 4:
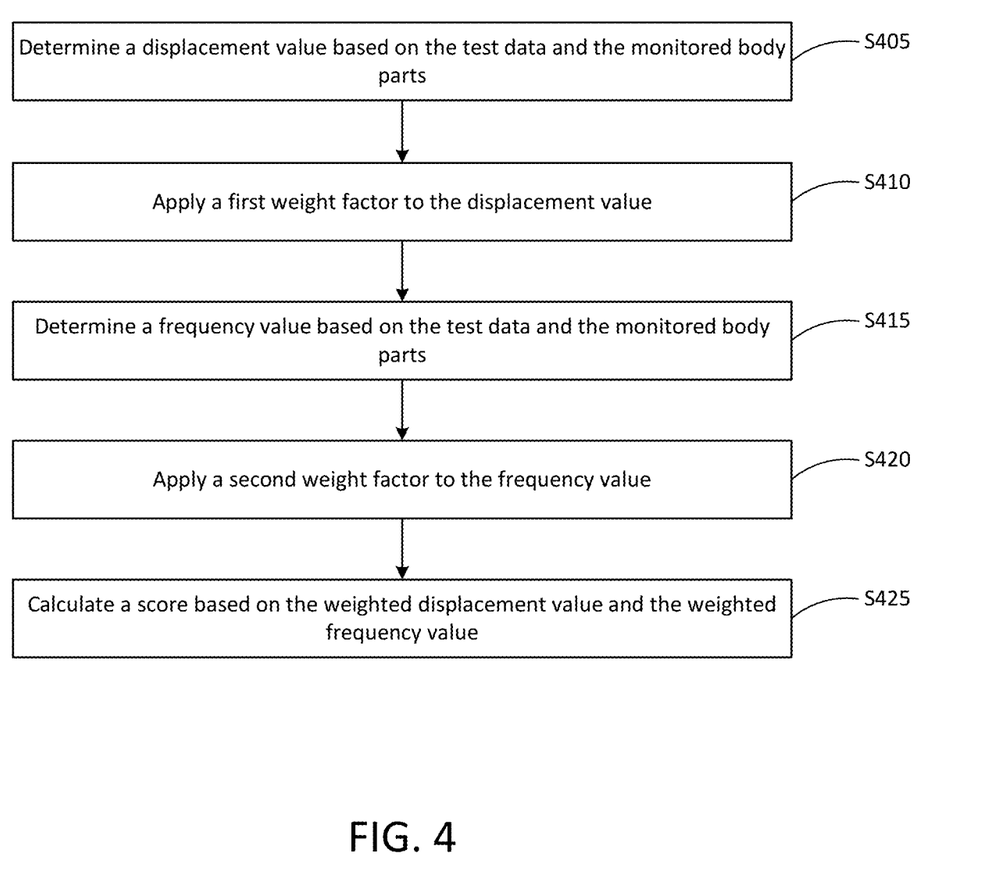
Figure 5:
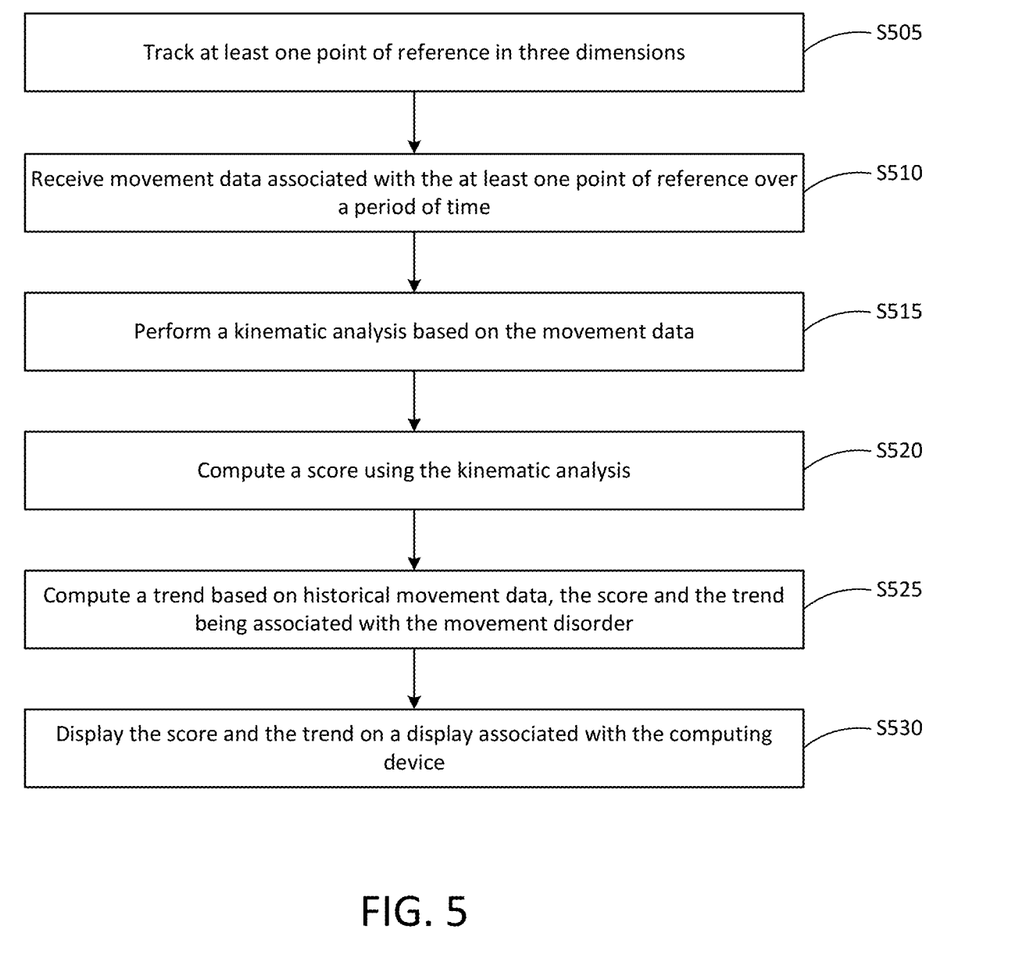

FIGS. 3-5 are flowcharts of methods according to example embodiments. The steps described with regard to FIGS. 3-5 may be performed due to the execution of software code stored in a memory (e.g., at least one memory 210) associated with an apparatus (e.g., as shown in FIGS. 1 and 2) and executed by at least one processor (e.g., at least one processor 205) associated with the apparatus. However, alternative embodiments are contemplated such as a system embodied as a special purpose processor. Although the steps described below are described as being executed by a processor, the steps are not necessarily executed by a same processor. In other words, at least one processor may execute the steps described below with regard to FIGS. 3-5.

In an example use case, an end user can download the software from Internet or other predetermined location. In some implementations, an end user can be a patient. However, an end user can be a clinician, a doctor, a technician, an IT representative, and/or the like. The software may be downloaded to the user's computer or tablet and a compatible movement detector (e.g., depth sensing camera) can be activated (S305). In some implementations, movement detector (e.g., depth sensors) can be communicatively coupled or attached to tablets using special connectors. In some implementations, the movement detector can communicate with the user's computer or tablet using a wired or wireless protocol.

In another example use case, the end user can implement the software through a web browser executed by the user's computer or tablet as a client device. The client device can receive code (e.g., HTML code) from a remote server (e.g., a remote server that hosts a website) and can execute the received code on the client device for the benefit of a user of the client device. The received code can be granted additional permissions to use local resources of the client computing device, beyond what typical code executed by a browser is permitted to use. For example, the received code can may access USB drives, BLUETOOTH devices, and/or access the local filesystem through operation of the web browser. Implementing the software through the web browser can include accessing a compatible movement detector (e.g., depth sensing camera). Then the compatible movement detector can be activated (S305). In some implementations, movement detector (e.g., depth sensors) can be communicatively coupled or attached to tablets using special connectors. In some implementations, the movement detector can communicate with the user's computer or tablet using a wired or wireless protocol.

In still another example use case, the web browser may include or have installed one or more web applications (or app). In this context, a web application may be configured to perform a single task or multiple tasks for the user. In such an implementation, the web application may be configured to be executed or interpreted by the web browser. Thus, web applications can be run inside a web browser with a dedicated user interface. The web application can be granted additional permissions to use local resources of the client computing device, beyond what typical code executed by a browser is permitted to use. For example, the web application can may access USB drives, BLUETOOTH devices, and/or access the local filesystem through operation of the web browser. Executing the web application can include accessing a compatible movement detector (e.g., depth sensing camera). Then the compatible movement detector can be activated (S305). In some implementations, movement detector (e.g., depth sensors) can be communicatively coupled or attached to tablets using special connectors. In some implementations, the movement detector can communicate with the user's computer or tablet using a wired or wireless protocol.

The system can be configured to calibrate the movement detector (S310), following a pre-programmed tutorial in the software. Most movement detectors (e.g., cameras) come with plug and play functions, and once the movement detector is correctly installed, the user can be directed to a log on page in order to log on to a profile server (S315). This log on can be through a Health Insurance Portability and Accountability Act (HIPAA) qualifying server that may allow the patient to securely access their profile or user profile (e.g., including tremor history data) on the system. This profile can be saved to their home computer (S320) and can be password and encryption protected. The patient can then be assigned a system ID that may be anonymized and can be shared with a physician or any other authorized person through an online portal to track patient progress over time. After accessing their profile for the first time, the user can be taken to a dashboard where their information, graphs and options are kept.

The system can be configured to enable the user to establish their basic information and personalize their profile (S325) or user profile. There can be prompts for all of the basic information regarding a patient, their current medication levels, and other relevant information with regards to the patient's medical conditions. According to example embodiments, the patient can designate the types of movement disorder(s) (S330) he or she wishes to track. Based on this information the software can select the appropriate tests that patient can have access to (S335). The software can be configured to automatically generate at least one test plan based on the user profile. In other words, the appropriate tests can be automatically packaged together to generate at least one test plan. A test plan can include one or more of the appropriate tests. The appropriate tests can be associated with a movement disorder.

The next step is to gather data and process the data (e.g., by the software). The patient can then be prompted to perform tests (S340). These tests may include, for example, postural tremor rating tests, kinetic tremor tests, resting tremor test, voice tremor tests, head and neck tremor tests, bradykinesia tests, dysdiadochokinesia tests, gait impediments, physiological tremors, epileptic symptoms, and any other test that is compatible with both the camera and the patient's disorders. For example, raw positional data (e.g., points in 3D space) can be collected from the movement detector 120 over a period of time. The raw positional data can be used to calculate metrics such as amplitude, frequency, and velocity associated with movement (e.g., tremor) of the patient. The raw positional data and/or the calculated metrics can be stored in the datastore 235.

The calculated metrics can be based on performing a kinematic data analysis on the raw positional data. For example, the kinematic data analysis can be an analysis of the movement data to generate measures that summarize major aspects of a patient's movement. Kinematic data analysis can include, but is not limited to, summary statistics (e.g., mean, standard deviation, and the like), power spectrum, numerical derivatives (e.g., obtain velocity, acceleration, jerk, and the like), numerical integrals, the number frequency and quality of actions, as just a few examples.

For example, the raw positional data can then be converted to a signal power (or amplitude) at different frequencies. For example, an averaged power spectrum can be generated using Welsh's method (or approach) to spectral density estimation. The primary tremor frequency can be the frequency on this spectrum that corresponds with the maximum (or peak) amplitude.

The primary frequency can be used to determine the tremor period. The raw positional data can be partitioned into non-overlapping segments that are two periods long. A displacement metric (e.g., 2*amplitude) associated with each segment can be the maximum distance between any two recorded body part (e.g., hand or finger) positions in a corresponding segment. The overall amplitude can be generated by averaging the segment amplitudes. In some implementations, outlier segment amplitudes may be discarded prior to averaging. Positional data at the beginning and end of the recording (e.g., when the user is placing or removing his hand) may also be discarded. Velocity can be determined indirectly by based on the amplitude and frequency. Alternatively, or in addition to, velocity may be calculated directly from the raw positional data.

Once the data is gathered the user can be shown several key figures and trends (S345). The first can be a rating of their tremor. The rating can be a score (e.g., between 0 and 100) indicative of quality of life. For example, a high score (e.g., closer to 100) indicates a higher quality of life and a low score (e.g., closer to 0) indicates a lower quality of life. Alternatively, and/or in addition to, the rating can be based on the standard test for patient care at that time and can employ the objective position in space data gathered by the computer, run through a low-pass filter to cancel out any intentional movement while being observed by the camera. For example, a band-pass filter may be applied to the power spectrum in order to remove low-frequency, large-scale translations in overall body part (e.g., hand o finger) movements. This same filter can also eliminate high-frequency tremors that are unlikely to be pathological.

As a user uses the system more frequently, the system can be configured to calibrate or hone in on the individual variances that the user exhibits in the patient's disorder and can be able to display that feature. Further, a graph showing the patients tremor over time can be displayed.

For example, a user may participate in a test at certain times of the day, or as patterns in ups and downs are identified. Calibrating or honing can include identifying patterns of tremor activity and prompting the end user to take an additional test(s) at a given time or under certain conditions. As a result, the observed trends can be confirmed through additional testing.

Each data point on the graph can be accessed and manipulated to show trends and progress over time. Users can isolate times when their medication was at certain levels and compare it to times when they didn't take their medication. This feature can also be more accurate, the more a patient uses the software, the more complete the data pool can be and the easier it can be to find outliers and trends in the patient's tremor. The software can also be configured to allow for a reconstruction of a tremor over time with a simple graphical representation that can plot the tremor on a line graph and follow it as it progresses. This feature can allow the user to see graphs that can be compared from different times and can allow them to see the details of their movement disorder. All data, graphs and reconstructions can be stored as an encrypted file that can only be accessed by the patient and their chosen medical provider. All data can be tracked over time and can be allowed to input medication levels, current ailments and other affecting factors to be entered and considered in the program. In any test where another object was needed to complete it, the user can use the object as describe by the software. As is necessary several instructional videos can be included to allow the user to see how to do any certain test.

FIG. 4 is a flowchart of a method for computing a score indicative of quality of life according to at least one example embodiment. As shown in FIG. 4, in step S405 a displacement value based on the test data and the monitored body parts is determined. For example, a displacement value (e.g., an amount or distance of movement) also referred to as amplitude or differential amplitude can be read from the datastore 235 for each (or a portion of) body part selected during software or test configuration (as described above). The displacement value can be a numeric value (e.g., in mm, cm, in, and/or the like). The displacement value can be based on a maximum or peak amplitude of a power spectrum based on movement data. The displacement value for a plurality of body parts can be summed together and an average displacement can be calculated. Alternatively, or in addition to, displacement for each of the plurality of body parts can be operated (e.g., used in a calculation) separately.

In step S410 a first weight factor is applied to the displacement value. For example, at least one of the displacement value, the summed displacement value and the average displacement value could be multiplied by the first weight factor. The first weight factor could be a pre-defined (e.g., configuration value) or a variable value (e.g., changed or modified over time) configured to scale at least one of the displacement value, the summed displacement value and the average displacement value.

In step S415 a frequency value is determined based on the test data and the monitored body parts. For example, a frequency value (e.g., how often a tremor movement lasts and/or how often a tremor movement occurs) can be read from the datastore 235 for each (or a portion of) body part selected during software or test configuration (as described above). The frequency value can be a numeric value (e.g., minutes, seconds, and/or the like). The frequency value can correspond to a frequency of a maximum or peak amplitude of a power spectrum based on movement data. The frequency value for a plurality of body parts can be summed together and an average total frequency can be calculated. Alternatively, or in addition to, total frequency for each of the plurality of body parts can be operated on (e.g., used in a calculation) separately.

In step S420 a second weight factor is applied to the frequency value. For example, at least one of the frequency value, the summed frequency value and the average frequency value could be multiplied by the second weight factor. The second weight factor could be a pre-defined (e.g., configuration value) or a variable value (e.g., changed or modified over time) configured to scale at least one of the total frequency value, the summed frequency value and the average frequency value. In an example implementation, the second weight factor is less than the first weight factor. In other words, the displacement value can be weighted heavier that the frequency value.

In step S425 a score (e.g., as a weighted score) is calculated based on the weighted displacement value and the weighted frequency value. For example, the weighted displacement value can be added to the weighted total frequency in order to calculate the score. The score can be calculated for a single body part, a portion of the configured body parts (e.g., body parts configured to be monitored) and/or all of the configured body parts.

In an example implementation, the score can be a number between 0 and 100. In addition, the displacement value and the frequency value each can be numbers normalized between 0 and 100 (noting that this disclosure is not limited to score, displacement and/or frequency scales between 0 and 100). Accordingly, when added together the displacement value and the total frequency value could result in a score greater than 100. Alternatively, the score can be normalized to between 0 and 100 after the score is calculated (e.g., without normalizing the displacement value and the frequency value). Therefore, the displacement value and the total frequency value are scaled or weighted. The scale or weighting can be fixed and constant (e.g., 60/40) or vary. For example, the displacement value weighting (or first weight factor) can vary up or down (e.g., between 0.5 and 1) based on the frequency of tremor (indicating quality of life). In other words, the displacement value weighting (or first weight factor) can vary up if the frequency of tremor is more often because a more frequent tremor indicates a lower quality of life.

According to example embodiments, different scoring methods can be utilized depending on the tests that are used. For example, tests that are monitoring for the amount of tremor a score can be computed as described above. However, tests utilizing interaction with points on the display of the computing device or an image on the display of the computing device, other mechanisms of quantification can be used. For example, speed of tremor, speed of movement, number of tasks completed (tapping, grasping or movements between predefined points) and/or deviation from a predetermined course of action can be used to calculate a score. Any number of factors or measurements may be used to (or help to) determine a person's score and can be plotted in a manner that will make it universally applicable across different patients and disorders.

FIG. 5 is a flowchart of a method for testing movement associated with a movement disorder according to at least one example embodiment. As shown in FIG. 5, in step S505 at least one point of reference is tracked in three dimensions. For example, raw positional data (e.g., points in 3D space) can be collected from the movement detector 120 over a period of time. According to an example implementation, the movement detector 120 can be a depth sensing camera, the at least one point of reference can include at least one of a finger, a plurality of fingers, a hand, a wrist, an arm, a head, a torso, and a leg. Further, the at least one point of reference may not include an attached marker, and/or the at least one point of reference may not include an attached sensor.

In step S510 movement data associated with the at least one point of reference over a period of time is received. For example, the raw positional data can be received by the computing device from a communicatively coupled movement detector 120. The period of time can be a time over which a movement disorder test is conducted. The movement data can be continuously (or substantially continuously) received and/or received in batches of data.

In step S515 a kinematic data analysis is performed based on the movement data. For example, the kinematic data analysis can be an analysis of the movement data to generate measures that summarize major aspects of a patient's movement. Kinematic data analysis can include, but is not limited to, summary statistics (e.g., mean, standard deviation, and the like), power spectrum, numerical derivatives (e.g., obtain velocity, acceleration, jerk, and the like), numerical integrals, the number frequency and quality of actions, as just a few examples.

For example, the raw positional data can then be converted to a signal power (or amplitude) at different frequencies. For example, an averaged power spectrum can be generated using Welsh's method (or approach) to spectral density estimation. The primary tremor frequency can be the frequency on this spectrum that corresponds with the maximum (or peak) amplitude.

In step S520 a weighted score is calculated using the kinematic data analysis. For example, the score can be indicative of quality of life of a patient. The score can be calculated as described in more detail above.

In step S525 a trend is calculated based on historical movement data, the weighted score and the trend being associated with a movement disorder. For example, as discussed above, the raw positional data, the data from the kinematic data analysis and/or the average power spectrum can be used to calculate metrics such as amplitude, displacement, frequency, and velocity associated with movement (e.g., tremor) of the patient. Values associated with the amplitude, displacement, frequency, and velocity can be stored (e.g., in datastore 235) in association with a patient. This stored historical movement data can be graphed (e.g., via functionality of the dashboard 215). Then, in step S530 the weighted score and the trend can be displayed on a display associated with a computing device (e.g., a computing device executing software including the dashboard 215). The display associated with the computing device can be remote to the computing device. In other words, the computing device can generate commands (e.g., lines of HTML or JAVA code) that will be communicated (e.g., via an internet or intranet) to a remote computing device for display using, for example, a web browser.

In addition, a replay of the movement data (representing tremor) and/or images captured with the raw movement data can be displayed on a display associated with a computing device. In other words, displaying information can include replaying the 3D data captured and showing the patient (or doctor or clinician) a rendering of what the tremor looks like.

In an example implementation data associated with tests as well as test results and user inputs can be communicated to a remote device and stored on the remote device. In another implementation, a remote device can have access and/or be configured to interface with a movement detector. Accordingly, a remote device can be configured to perform the techniques described herein where the patient and the computing device are not co-located.

The system of the example embodiment described above and accompanying algorithms could also be applied to any other specific industry where movement of people or objects would need to be analyzed over time. The algorithms in our software can be adjusted according to follow these applications as well. For example, police could use the software to monitor intoxicated drivers from a car; a system could be designed to aid in security at airports or sporting events. The applications are only limited to the scale of what movement the user wants to track over time. This system does not impede the natural movements exhibited by the patients due to the marker-less design. The system also gives physicians and other users a tool to track progression of these progressive diseases that are not currently in a configurable tool for all patients and all types of movement disorders.

Another benefit may be that this system would enable testing in situations where a direct position in space vs. time data would allow for the most intuitive and straightforward system for the patient. Another advantage is that there is no set-up or application of accelerometers in our system. Other systems, have highly involved calibration and installment steps that make the difficult to use.

Some of the above example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed above, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks may be stored in a machine or computer readable medium such as a storage medium and/or a non-transitory computer readable medium. A processor(s) (e.g., a silicon or GaAs based processor) may perform the necessary tasks.

Specific structural and functional details disclosed herein are merely representative for purposes of describing example embodiments. Example embodiments, however, be embodied in many alternate forms and should not be construed as limited to only the embodiments set forth herein.

It can be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term and/or includes any and all combinations of one or more of the associated listed items.

It can be understood that when an element is referred to as being connected or coupled to another element, it can be directly connected or coupled to the other element or intervening elements may be present. In contrast, when an element is referred to as being directly connected or directly coupled to another element, there are no intervening elements present. Other words used to describe the relationship between elements should be interpreted in a like fashion (e.g., between versus directly between, adjacent versus directly adjacent, etc.).

The terminology used herein is for the purpose of describing particular embodiments only and is not intended to be limiting of example embodiments. As used herein, the singular forms a, an, and the, are intended to include the plural forms as well, unless the context clearly indicates otherwise. It can be further understood that the terms comprises, comprising, includes and/or including, when used herein, specify the presence of stated features, integers, steps, operations, elements and/or components, but do not preclude the presence or addition of one or more other features, integers, steps, operations, elements, components and/or groups thereof.

It should also be noted that in some alternative implementations, the functions/acts noted may occur out of the order noted in the figures. For example, two figures shown in succession may in fact be executed concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It can be further understood that terms, e.g., those defined in commonly used dictionaries, should be interpreted as having a meaning that is consistent with their meaning in the context of the relevant art and can not be interpreted in an idealized or overly formal sense unless expressly so defined herein.

Portions of the above example embodiments and corresponding detailed description are presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the above illustrative embodiments, reference to acts and symbolic representations of operations (e.g., in the form of flowcharts) that may be implemented as program modules or functional processes include routines, programs, objects, components, data structures, etc., that perform particular tasks or implement particular abstract data types and may be described and/or implemented using existing hardware at existing structural elements. Such existing hardware may include one or more Central Processing Units (CPUs), digital signal processors (DSPs), application-specific-integrated-circuits, field programmable gate arrays (FPGAs) computers or the like.

It should be borne in mind, however, that all of these and similar terms are to be associated with the appropriate physical quantities and are merely convenient labels applied to these quantities. Unless specifically stated otherwise, or as is apparent from the discussion, terms such as processing or computing or calculating or determining of displaying or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Note also that the software implemented aspects of the example embodiments are typically encoded on some form of non-transitory program storage medium or implemented over some type of transmission medium. The program storage medium may be magnetic (e.g., a floppy disk or a hard drive) or optical (e.g., a compact disk read only memory, or CD ROM), and may be read only or random access. Similarly, the transmission medium may be twisted wire pairs, coaxial cable, optical fiber, or some other suitable transmission medium known to the art. The example embodiments not limited by these aspects of any given implementation.

Lastly, it should also be noted that whilst particular combinations of features described herein, the scope of the present disclosure is not limited to the particular combinations, but instead extends to encompass any combination of features or embodiments herein disclosed irrespective of whether or not that particular combination has been specifically enumerated.

Lastly, it should also be noted that whilst the accompanying claims set out particular combinations of features described herein, the scope of the present disclosure is not limited to the particular combinations hereafter claimed, but instead extends to encompass any combination of features or embodiments herein disclosed irrespective of whether or not that particular combination has been specifically enumerated in the accompanying claims at this time.

What is claimed is:

1. A system for monitoring a movement disorder, the system comprising:
   a movement detector configured to track, using three-dimensional data, at least one point of reference;
   a computing device configured to communicate with the movement detector, the computing device configured to:
   receive movement data associated with an individual diagnosed with the movement disorder and with the at least one point of reference over a period of time, perform a kinematic data analysis based on the movement data including generating an averaging segmented amplitudes of a spectrum power of the movement data and selecting a primary tremor frequency, compute a weighted score indicative of a severity of the movement disorder, the computing the weighted score including:
   computing an amplitude based on the kinematic data analysis, computing a displacement based on the amplitude, computing a frequency based on the kinematic data analysis,
   and computing the weighted score based on the displacement and the frequency, compute a trend associated with the individual diagnosed with the movement disorder based on historical movement data, the weighted score and the trend being associated with the movement disorder, and
   trigger display of the weighted score, the trend, and the movement data on a display associated with the computing device to indicate a severity of the movement disorder based on the kinematic data analysis; and
   a movement disorder interface configured to perform a calibration routine, the calibration routine including:
   identifying a pattern and a variance associated with the movement disorder,
   prompting to perform an additional test at least one of at a given time or under a condition,
   confirming the pattern for use in tracking the diagnosed movement disorder based on the additional test, and
   displaying said pattern and said variance over time.

2. The system of claim 1, wherein the movement detector is a depth sensing camera, the three-dimensional data including depth data.

3. The system of claim 1, wherein the at least one point of reference includes at least one of a finger, a plurality of fingers, a hand, a wrist, an arm, a head, a torso, and a leg.

4. The system of claim 1, wherein the computing device is further configured to compute a velocity of movement based on the kinematic data analysis.

5. The system of claim 1, wherein the computing device includes a dashboard implemented as an element of a software package, the dashboard being configured to:
   initiate and select a test associated with at least one movement disorder;
   after the test has been completed, display results including at least the weighted score and the trend; and
   control access to data of a user.

6. The system of claim 1, wherein
   the computing device is configured to allow a user to generate a user profile including information associated with at least one movement disorder, and
   the computing device is configured to generate at least one test plan based on the user profile.

7. The system of claim 1, wherein
   computing the displacement includes computing a weighted displacement,
   computing the frequency includes computing a weighted frequency, and
   the weighted score is based on the weighted displacement and the weighted frequency.

8. The system of claim 1, wherein computing the displacement includes computing a normalized displacement,
   computing the frequency includes computing a normalized frequency, and
   the weighted score is based on the normalized displacement and the normalized frequency.

9. The system of claim 1, wherein the historical movement data is associated with a plurality of patients.

10. The system of claim 1, wherein the weighted score is a normalized score comparable to data associated with a plurality of patients.

11. The system of claim 1, wherein the weighted score is a normalized score universally comparable to data associated with a plurality of patients and a plurality of disorders.

12. An apparatus, comprising:
    a movement detector configured to track at least one point of reference in three dimensions including an x dimension, a y dimension, and a z dimension;
    a computing device configured to communicate with the movement detector, the computing device configured to:
    receive movement data associated with an individual diagnosed with the a movement disorder and with the at least one point of reference over a period of time, perform a kinematic data analysis based on the movement data including generating an averaging segmented amplitudes of a spectrum power of the movement data and selecting a primary tremor frequency, determine a normalized displacement value and a normalized frequency value associated with the at least one point of reference over the period of time based on the kinematic data analysis such that the normalized displacement value and the normalized frequency value are comparable to data associated with a plurality of patients, comparing the normalized displacement and the normalized frequency with a historical trend of movement data associated with the individual diagnosed with the movement disorder, and
    in response to the comparison, prompting a user associated with the received movement data to collect additional movement data; and
    a movement disorder interface configured to perform a calibration routine, the calibration routine including:

identifying a pattern and a variance associated with the movement disorder, prompting to perform an additional test at least one of at a given time or under a condition, confirming the pattern for use in tracking the diagnosed movement disorder based on the additional test, and displaying said pattern and said variance over time.

13. The apparatus of claim 12, wherein the movement detector is a depth sensing camera configured to produce an output used to define the x dimension, the y dimension, and the z dimension.

14. The apparatus of claim 12, wherein the kinematic data analysis includes determining at least one of a displacement value or a frequency value based on the movement data.

15. The apparatus of claim 12, wherein the computing device is further configured to compute metrics including a velocity based on the kinematic data analysis.

16. An apparatus for monitoring a movement disorder, the apparatus comprising:

a movement detector configured to track, using three-dimensional data, at least one point of reference;

a computing device configured to communicate with the movement detector, the computing device configured to:

receive movement data associated with an individual diagnosed with the movement disorder and with the at least one point of reference over a period of time, filter the received movement data to isolate movement data associated with the movement disorder, perform a kinematic data analysis of the filtered movement data, including determining at least one of a displacement value or a frequency value, based on the movement data including generating an averaging segmented amplitudes of a spectrum power of the movement data and selecting a primary tremor frequency, determine a normalized score using the kinematic data analysis, the normalized score being comparable to data associated with at least one of a plurality of patients or a plurality of disorders, and trigger display of the normalized score on a display associated with the computing device to indicate a severity of the movement data associated with the movement disorder; and a movement disorder interface configured to perform a calibration routine, the calibration routine including:

identifying a pattern and a variance associated with the movement disorder, prompting to perform an additional test at least one of at a given time or under a condition, confirming the pattern for use in tracking the diagnosed movement disorder based on the additional test, and displaying said pattern and said variance over time.

17. The apparatus of claim 16, wherein the movement detector is a depth sensing camera.

18. The apparatus of claim 16, wherein the at least one point of reference includes at least one of a finger, a plurality of fingers, a hand, a wrist, an arm, a head, a torso, and a leg.

19. The apparatus of claim 16, wherein the kinematic data analysis includes determining both a displacement value and a frequency value.

20. The apparatus of claim 16, wherein the filtering the received movement data includes removing at least one of movement data associated with intentional movement or movement data associated with tremors.

* * * * *